US00PP36782P2

(12) United States Plant Patent
Sills et al.

(10) Patent No.: US PP36,782 P2
(45) Date of Patent: Jul. 1, 2025

(54) BLACKBERRY PLANT NAMED 'DrisBlackThirtyFive'

(50) Latin Name: ***Rubus* L. subgenus Rubus.**
Varietal Denomination: DrisBlackThirtyFive

(71) Applicant: Driscoll's, Inc., Watsonville, CA (US)

(72) Inventors: Gavin R. Sills, Gilroy, CA (US); Yunwen Wang, Aptos, CA (US); Mark F. Crusha, Santa Cruz, CA (US); John Nader Fangary, Royal Oaks, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 18/931,660

(22) Filed: Oct. 30, 2024

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./156, 203
See application file for complete search history.

(56) References Cited

U.S. PATENT DOCUMENTS

PP6,679 P 3/1989 Moore
PP6,782 P 5/1989 Jennings
PP13,525 P3 1/2003 Fear et al.
PP13,758 P3 5/2003 Fear et al.
PP13,759 P3 5/2003 Fear et al.
PP14,682 P3 4/2004 Fear et al.
PP14,765 P2 5/2004 Cook et al.
PP14,780 P2 * 5/2004 Fear ..... A01H 6/7499 Plt./203
PP15,058 P2 8/2004 Cook et al.
PP17,162 P3 10/2006 Moore et al.
PP17,983 P2 9/2007 Cabrera
PP22,002 P2 7/2011 Pabon et al.
PP22,449 P3 1/2012 Clark
PP23,497 P3 3/2013 Clark et al.
PP23,725 P3 7/2013 Sills et al.
PP24,249 P3 2/2014 Clark
PP24,609 P3 7/2014 Rodriguez et al.
PP24,701 P3 7/2014 Rodriguez et al.
PP24,878 P2 9/2014 Alcazar et al.
PP25,502 P3 * 5/2015 Sills ..... A01H 6/7499 Plt./203
PP26,501 P3 3/2016 Pabon et al.
PP26,611 P3 4/2016 Pabon et al.
PP26,774 P3 5/2016 Pabon et al.
PP27,129 P2 9/2016 Sills et al.
PP27,130 P2 9/2016 Sills et al.
PP27,146 P2 9/2016 Sills et al.
PP27,681 P3 2/2017 Sills et al.
PP27,746 P3 3/2017 Sills et al.
PP28,548 P2 10/2017 Sills et al.
PP31,110 P2 11/2019 Sills et al.
PP31,291 P2 12/2019 Sills et al.
PP31,825 P2 6/2020 Sills et al.
PP31,826 P2 6/2020 Sills et al.
PP32,268 P2 10/2020 Sills et al.
PP33,067 P2 5/2021 Sills et al.
PP33,068 P2 5/2021 Sills et al.
PP33,088 P2 5/2021 Sills et al.
PP34,069 P2 3/2022 Sills et al.
PP34,291 P2 6/2022 Sills et al.
PP34,320 P2 6/2022 Escobedo et al.
PP34,438 P2 7/2022 Sills et al.
PP34,481 P2 8/2022 Sills et al.
PP35,078 P2 4/2023 Sills et al.
PP35,233 P2 6/2023 Sills et al.
PP35,898 P2 7/2024 Sills et al.
PP36,300 P2 * 12/2024 Sills ..... Plt./203

OTHER PUBLICATIONS

Voss, Donald H. The Royal Horticultural Society Colour Chart 2001 Journal American Rhododendron Society, vol. 56, No. 1 2002 3 pages.

Williams, et al. DNA polymorphisms amplified by arbitrary primers are useful as genetic markers Nucleic Acids Research, vol. 18, No. 22 1990 pp. 6531-6535.

* cited by examiner

*Primary Examiner* — Karen M Redden
(74) *Attorney, Agent, or Firm* — Morrison & Foerster LLP

(57) ABSTRACT

A new and distinct variety of blackberry plant named 'DrisBlackThirtyFive', particularly selected for its plant health, the size, firmness, and flavor of fruit, and spineless canes, is disclosed.

5 Drawing Sheets

Latin name: Botanical classification: *Rubus* L. subgenus *Rubus*.

Varietal denomination: The varietal denomination of the claimed variety of blackberry plant is 'DrisBlackThirty-Five'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed that are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackThirtyFive'.

Blackberry plant variety 'DrisBlackThirtyFive' was selected in Santa Cruz County, California in July 2018 and originated from a controlled cross between the female parent proprietary blackberry plant 'BT370.1' (unpatented) and the male parent blackberry plant 'DrisBlackTwentyThree' (U.S. Plant Pat. No. 33,067). The original seedling of the new variety was first asexually propagated via root cuttings in Santa Cruz County, California in October 2018.

'DrisBlackThirtyFive' was subsequently asexually propagated and underwent testing in Santa Cruz County, California from 2019 to 2023 (four years). The present variety has been found to be stable and reproduce true to type through successive asexual propagations via root cuttings and tissue culture.

'DrisBlackThirtyFive' was selected for its plant health, the size, firmness, and flavor of fruit, and spineless canes.

BRIEF DESCRIPTION OF THE DRAWINGS

This new blackberry plant is illustrated by the accompanying photographs. The colors shown are as true as can be reasonably obtained by conventional photographic procedures. The photographs are of plants that are two to five years old.

DETAILED BOTANICAL DESCRIPTION

Figure 1:
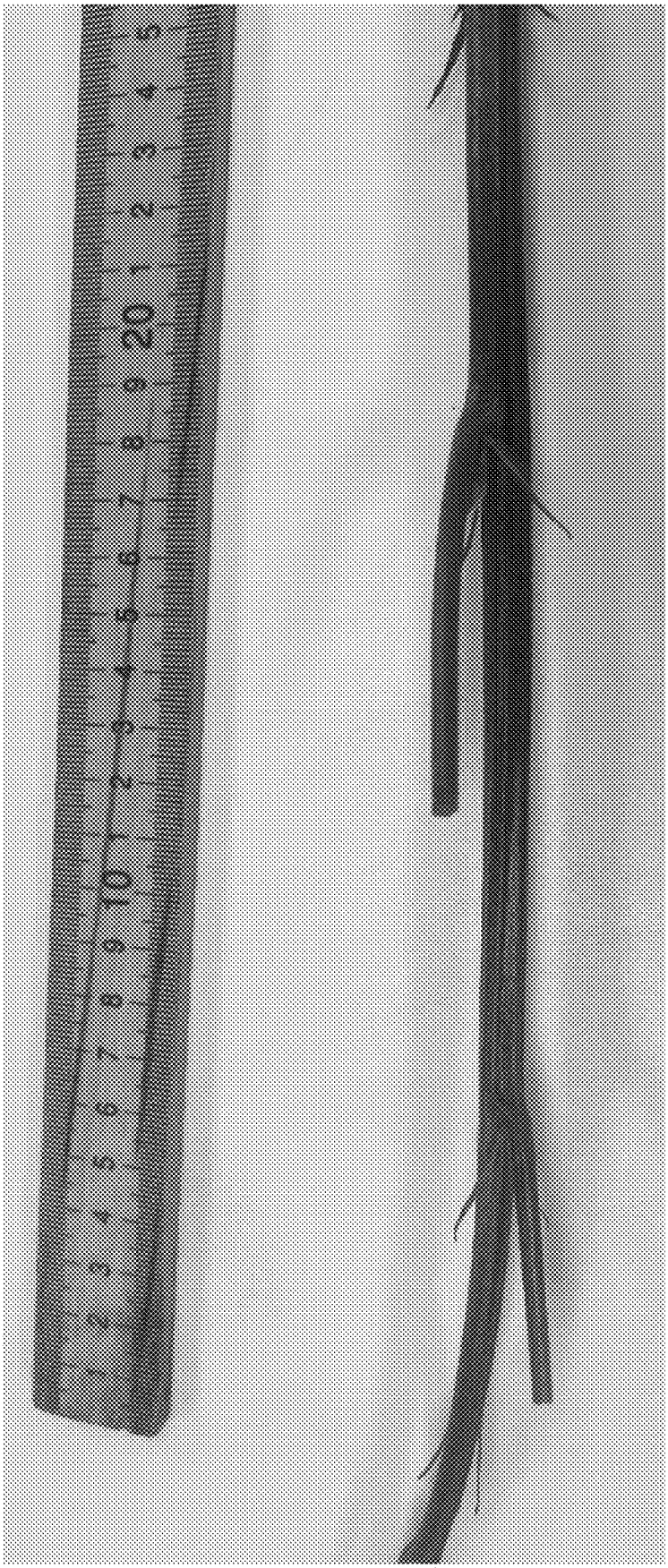
FIG. 1 illustrates a section of a cane of variety 'DrisBlackThirtyFive'.
Figure 2:
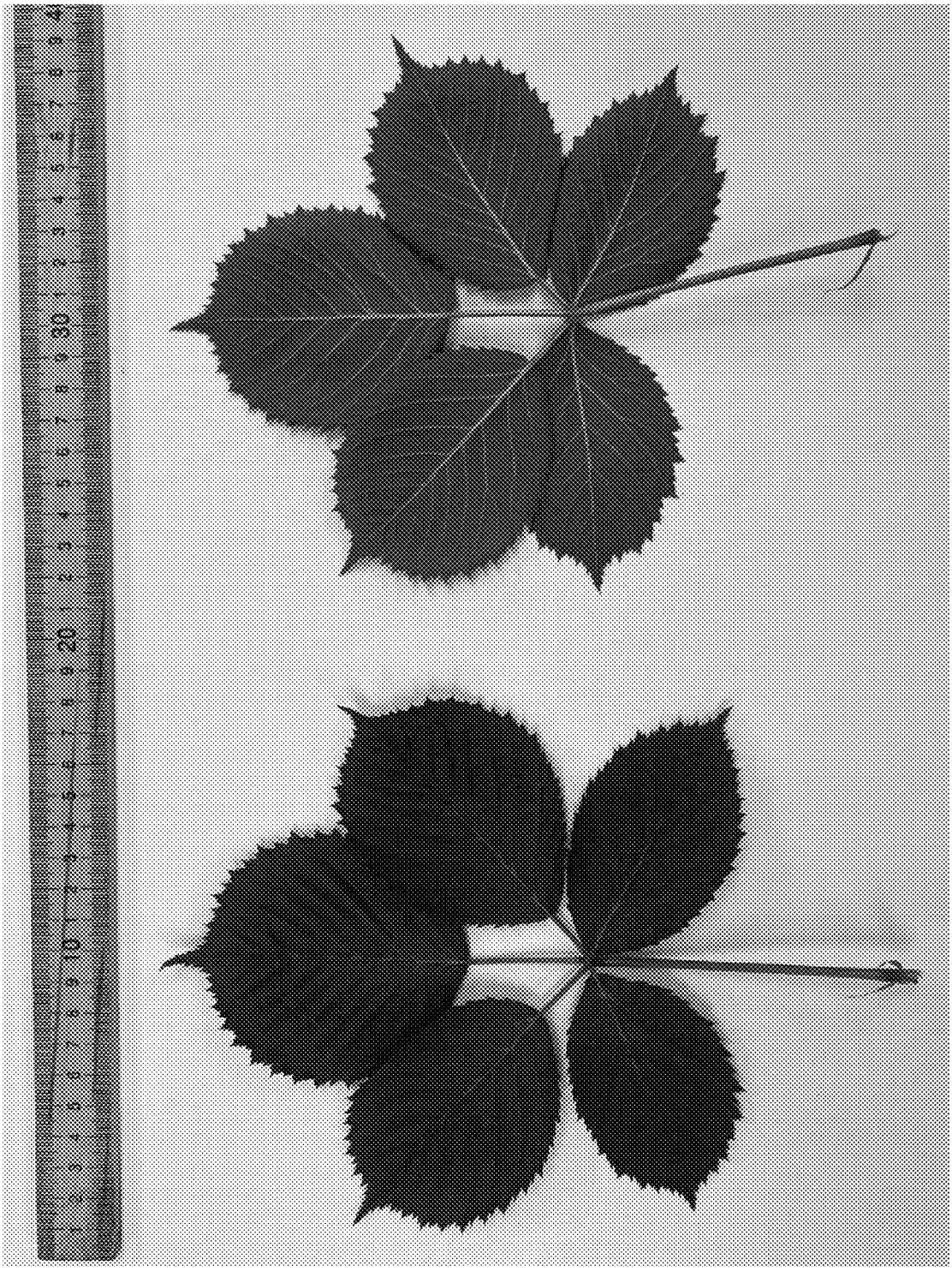
FIG. 2 illustrates the upper (left) and lower (right) surface of leaves of variety 'DrisBlackThirtyFive'.
Figure 3:
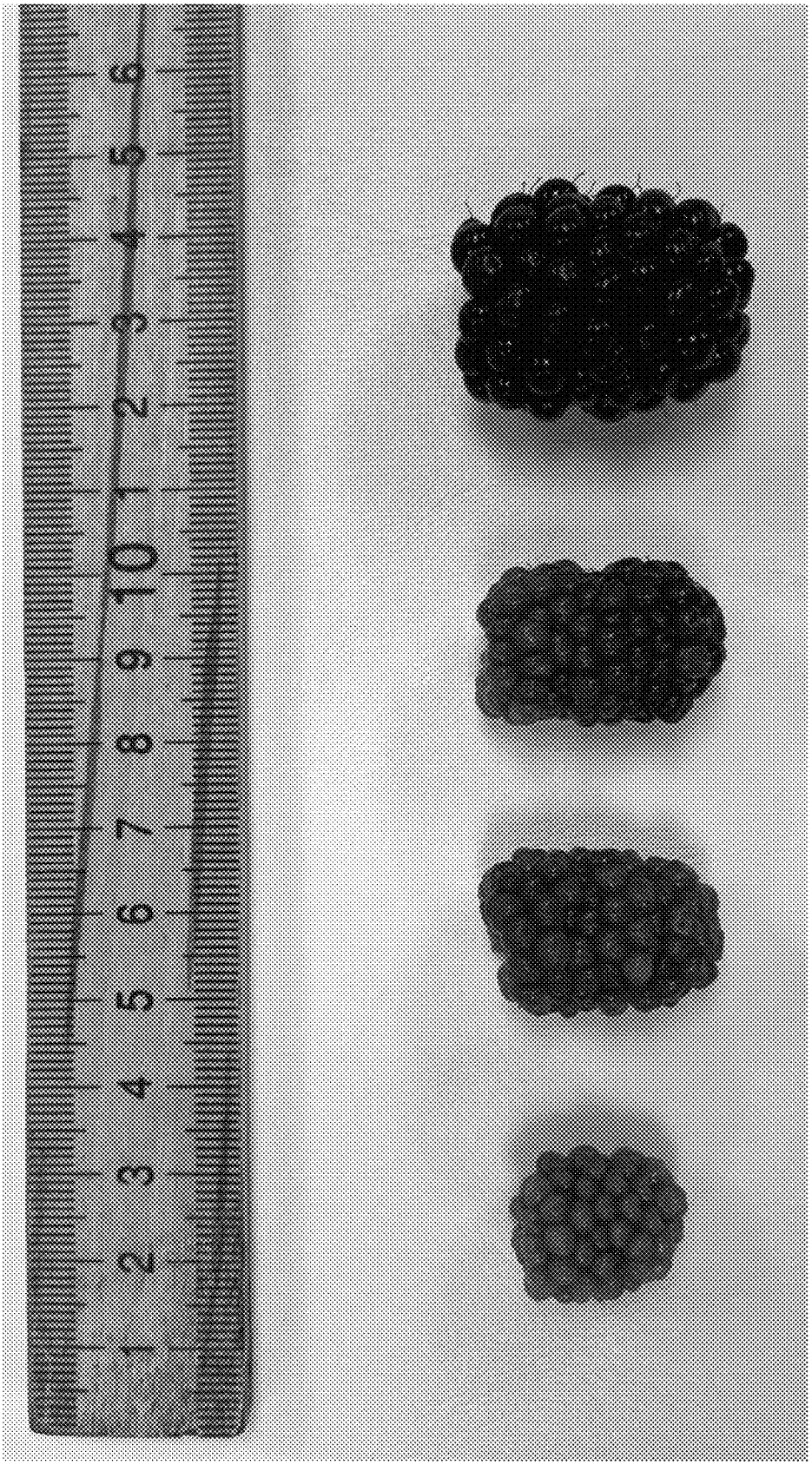
FIG. 3 illustrates fruits of variety 'DrisBlackThirtyFive' at various stages of development.
Figure 4:
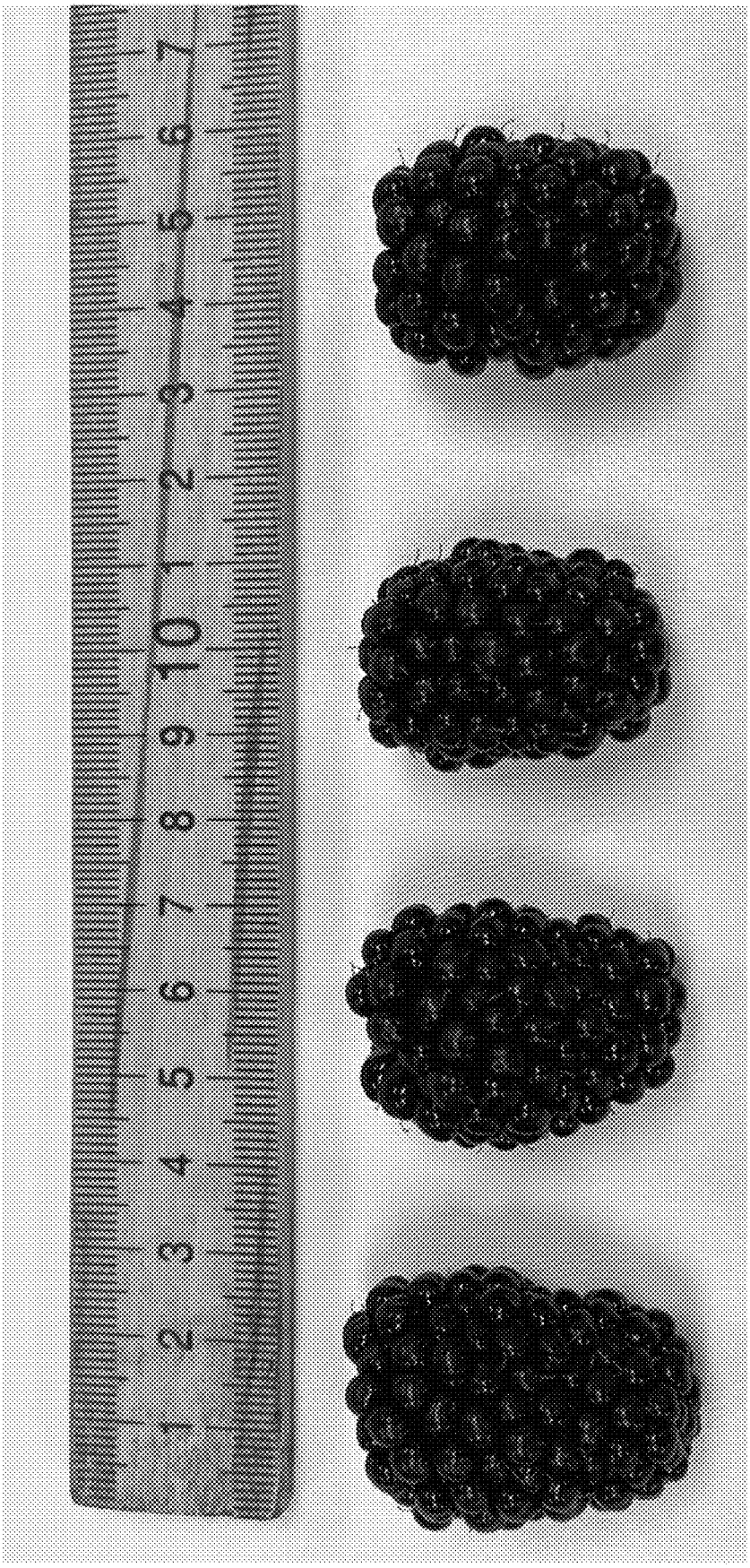
FIG. 4 illustrates ripe fruits of variety 'DrisBlackThirtyFive'.
Figure 5:
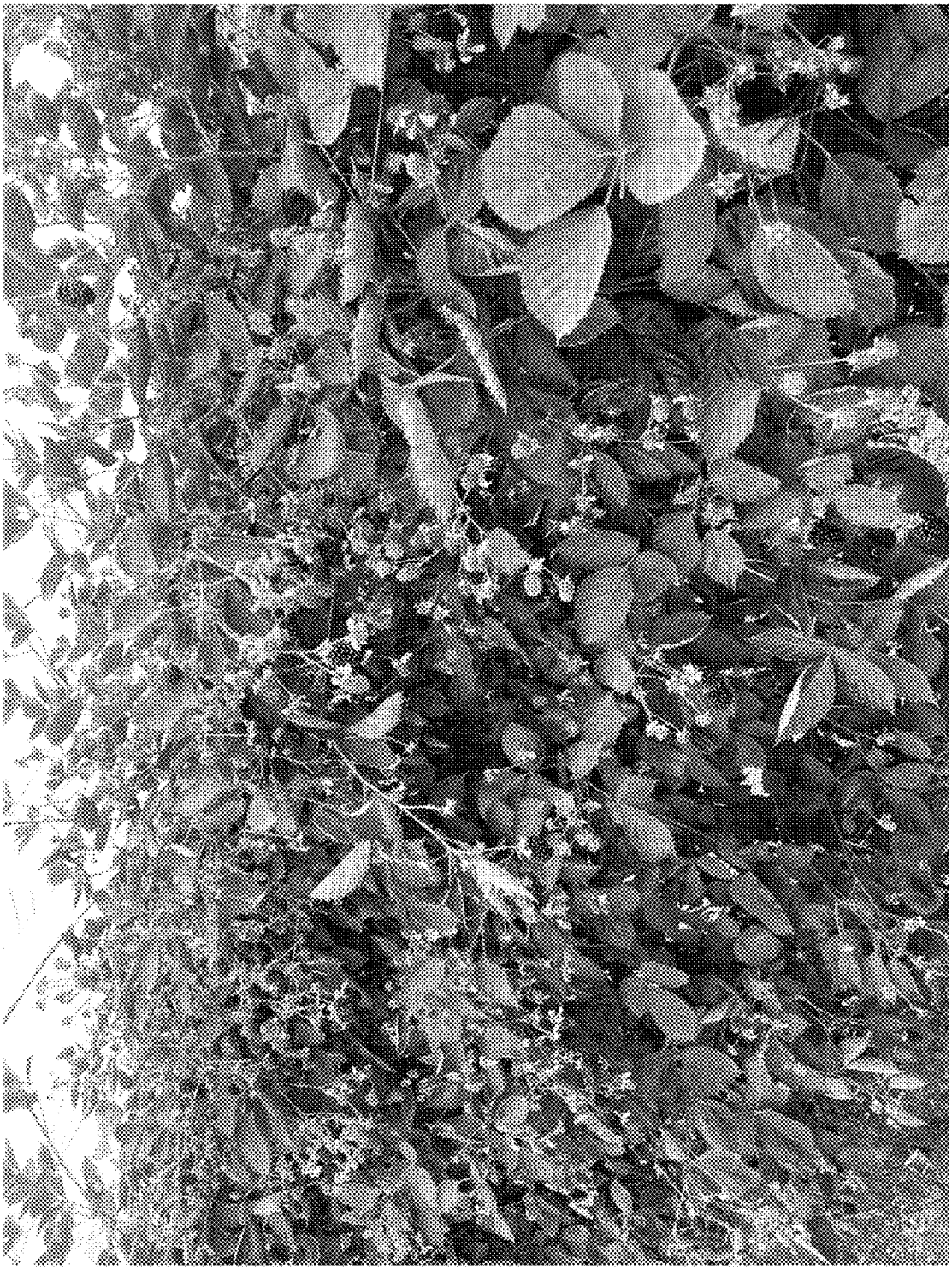
FIG. 5 illustrates a whole plant of variety 'DrisBlackThirtyFive'.

The following descriptions set forth the distinctive characteristics of 'DrisBlackThirtyFive'. The data that define these characteristics are based on observations taken in Santa Cruz County, California from 2019 to 2023. This description is in accordance with UPOV terminology. Color designations, color descriptions, and other phenotypical descriptions may deviate from the stated values and descriptions depending upon variation in environmental, seasonal, climatic and cultural conditions. 'DrisBlackThirtyFive' has not been observed under all possible environmental conditions. The botanical description of 'DrisBlackThirtyFive' was taken from plants that were two to five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.

*Botanical*.—*Rubus* L. subgenus *Rubus*.

*Common name*.—Blackberry.

*Variety name*.—'DrisBlackThirtyFive'.

Parentage:

*Female parent*.—Proprietary blackberry plant 'BT370.1' (unpatented).

*Male parent*.—'DrisBlackTwentyThree' (U.S. Plant Pat. No. 33,067).

Plant:

*Propagation*.—Root cuttings and tissue culture.

*Growth habit*.—Upright.

*Height*.—168 cm.

*Width*.—89 cm.

*Height/width ratio*.—1.89.

*Vigor*.—Medium.

*Self-fruitfulness*.—Self-fruitful.

Canes:

*Internodal distance*.—7.8 cm.

*New cane*.—Strength: Medium. Glaucosity (waxy bloom): Medium.

*Dormant cane*.—Anthocyanin coloration: Medium. Overall coloration: RHS 144A (Yellow-green). Predominant distribution of branches: Over whole length. Cross-section: Angular to grooved. Spine: Presence of spines: Absent.

*Fruiting lateral*.—Fruiting lateral length (4$^{th}$ lateral from tip): 59 cm. Number of fruits per fruiting lateral: 18.

*Young shoots*.—Length: 264 cm. Diameter: 1 cm. Anthocyanin coloration (during rapid growth): Medium. Overall color: RHS 143A (Strong yellow). Number of glandular hairs: Absent or few. Time of young shoot emergence: March to June.

Leaves:

*Time of leaf bud burst*.—Early March.

*Leaf*.—Predominant number of leaflets: Five (5). Type: Palmate. Relative position of lateral leaflets: Free. Arrangement: Whorled. Venation: Cross-venulate. Vein color: RHS 144C (Yellow green). Color of upper side: RHS 139A (Dark yellow green). Color of lower side: RHS 146A (Moderate olive green). Profile in cross-section: Flat (level with the leaflet blade). Glossiness of upper side: Medium.

*Leaflet*.—Type of incision of margin: Bi-serrate. Depth of margin incisions: Medium.

*Terminal leaflet*.—Length: 10.5 cm. Width: 9.6 cm. Length/width ratio: 1.09. Shape: Orbicular. Apex: Acuminate. Base: Obtuse. Margin: Doubly serrate. Lobing: Absent. Shape in cross-section: U-shaped. Undulation of margin: Absent or very weak. Blistering between veins: Weak.

*Lateral leaflet* (*single leaflet in basal pair*).—Length: 9.2 cm. Width: 6.8 cm. Length/width ratio: 1.35. Shape: Oval. Apex: Acuminate. Base: Obtuse. Margin: Doubly serrate.

*Rachis* (*length between terminal leaflet and adjacent lateral leaflets*).—3.5 cm.

*Petiole*.—Length: 8.4 cm. Diameter: 2 mm. Color of upper surface: RHS 138B (Moderate yellow green).

*Stipule*.—Length: 1.9 cm. Width: 1 mm. Color: RHS NN137A (Greyish olive green). Orientation: Erect.

Inflorescence:

*Flower bud*.—Length: 8 mm. Width: 7.4 mm. Color: RHS 143C (Strong yellow green).

*Flower*.—Diameter: 29.4 mm. Number of flowers observed at 3$^{rd}$ node from tip of lateral: 4. Fragrance: Very faint or absent.

*Petal*.—Length: 14.9 mm. Width: 13.2 mm. Length/width ratio: 1.13. Number of petals per flower: 5.4. Color: RHS 69D (Very pale purple). Shape: Oval. Apex: Rounded. Base: Obtuse. Margin: Erose.

*Sepal*.—Length: 7.8 mm. Width: 5.1 mm. Color: RHS 143B (Strong yellow green).

*Flower pedicel*.—Length: 54.3 mm. Diameter: 2 mm. Color: RHS 143A (Strong yellow green).

*Inflorescence peduncle*.—Length: 75 mm. Diameter: 2 mm. Color: RHS 143A (Strong yellow green).

*Reproductive organs*.—Style: Length: 2 mm. Color: RHS 144C (Strong yellow green). Ovary: Color: RHS 144A (Strong yellow green). Stamen: Length: 6.54 mm. Color: RHS 144B (Strong yellow green). Pollen: Amount: Medium. Color: RHS 145C (Light yellow green).

*Flowering interval on previous year's cane* (*floricane*).—Mid-May to mid-June.

Fruit:

*Length of mature fruit*.—31.6 mm.

*Diameter of mature fruit*.—24 mm.

*Ratio of length to width*.—1.32.

*Floricane fruit weight*.—10 g/fruit.

*Sweetness/soluble solids* (*in ° brix*).—14.

*Titratable acidity* (*% as citric acid*).—1.7%.

*Glossiness*.—Medium.

*Firmness*.—Medium firm.

*Fruit shape in longitudinal section*.—Oblong.

*Fruit color*.—RHS 203A (Black).

*Drupe*.—Length of single drupe: 5 mm. Diameter of single drupe: 5 mm. Average number of drupes per fruit: 100.

*Seed*.—Diameter: 1 mm. Weight: 0.00296 g/seed. Color: RHS 156A (Greyed-white). Abundance: Medium.

*Fruiting on current year's cane*.—Absent.

*Harvest interval on previous year's cane* (*floricane*).—June to mid-August.

*Yield*.—16,000 lbs to 20,000 lbs of fruit per acre per season from 24- to 36-month-old plants when grown in Watsonville, California.

Resistance to pests and diseases:

*Redberry mite* (*acalitus essigi*).—Moderately susceptible.

*Fusarium wilt* (*fusarium oxysporum*).—Resistant.

*Verticillium wilt* (*verticillium spp*.).—Susceptible.

COMPARISON TO PARENTAL AND REFERENCE BLACKBERRY VARIETIES

'DrisBlackThirtyFive' differs from the female parent proprietary blackberry plant 'BT370.1' (unpatented) in that 'DrisBlackThirtyFive' has larger fruit size and higher yield potential than 'BT370.1'.

'DrisBlackThirtyFive' differs from the male parent 'DrisBlackTwentyThree' (U.S. Plant Pat. No. 33,067) in that 'DrisBlackThirtyFive' has medium anthocyanin coloration on dormant cane, angular to grooved cross section of dormant cane, oblong shape of fruit in longitudinal section, and the color of flower petals is white with violet tinge, whereas 'DrisBlackTwentyThree' has strong anthocyanin coloration on dormant cane, rounded to angular cross section of dormant cane, elliptic shape of fruit in longitudinal section, and the color of flower petals is white.

'DrisBlackThirtyFive' differs from the reference variety 'DrisBlackSix' (U.S. Plant Pat. No. 25,502) in that 'DrisBlackThirtyFive' has an upright growth habit, medium anthocyanin coloration on dormant cane, angular to grooved cross section of dormant cane, and oblong shape of fruit in longitudinal section, whereas 'DrisBlackSix' has a semi-upright growth habit, strong anthocyanin coloration on dormant cane, rounded to angular cross section of dormant cane, and narrow ovate shape of fruit in longitudinal section.

What is claimed is:

1. A new and distinct variety of blackberry plant designated 'DrisBlackThirtyFive' as shown and described herein.

* * * * *